US012491332B2

(12) United States Patent
Chen et al.

(10) Patent No.: US 12,491,332 B2
(45) Date of Patent: Dec. 9, 2025

(54) OSCILLATING POSITIVE EXPIRATORY PRESSURE DEVICE

(71) Applicant: ENCHANT TEK. CO., LTD., Dongshan Township, Yilan County (TW)

(72) Inventors: Chun-Hung Chen, Dongshan Township, Yilan County (TW); Ling-Ling Leonard Lin, Dongshan Township, Yilan County (TW); Min-Hsien Huang, Dongshan Township, Yilan County (TW)

(73) Assignee: ENCHANT TEK. CO., LTD., Dongshan Township (TW)

( * ) Notice: Subject to any disclaimer, the term of this patent is extended or adjusted under 35 U.S.C. 154(b) by 813 days.

(21) Appl. No.: 17/835,670

(22) Filed: Jun. 8, 2022

(65) Prior Publication Data

US 2022/0395666 A1 Dec. 15, 2022

(30) Foreign Application Priority Data

Jun. 15, 2021 (TW) ................................ 110121639

(51) Int. Cl.
*A61M 16/20* (2006.01)
*A61M 16/00* (2006.01)

(52) U.S. Cl.
CPC ...... *A61M 16/208* (2013.01); *A61M 16/0006* (2014.02)

(58) Field of Classification Search
CPC .............. A61M 16/208; A61M 16/209; A61M 16/0006; A61M 16/0866; A61M 2206/14; A63B 21/00058; A63B 21/00196; A63B 21/0085; A63B 23/18
See application file for complete search history.

(56) References Cited

U.S. PATENT DOCUMENTS

2003/0226562 A1* 12/2003 Schmidt ............ A61M 16/0858 128/200.24
2003/0234017 A1* 12/2003 Pelerossi ............. A61M 16/205 128/201.28
2008/0078383 A1* 4/2008 Richards ............... A61M 16/08 128/203.12
2022/0313930 A1* 10/2022 Hsiung ................. A61M 16/20

* cited by examiner

*Primary Examiner* — Elliot S Ruddie
(74) *Attorney, Agent, or Firm* — HSML P.C.

(57) ABSTRACT

An oscillating positive expiratory pressure device includes a housing, a top cover, and an oscillating unit. The housing includes a bottom wall and a surrounding wall. The bottom wall has an inclined enclosing surface extending downwardly and terminating at an opening. The oscillating unit is swingably connected to and disposed within the housing. The oscillating unit includes a swing member, and first and second weighting pieces. The swing member includes a swing arm, and first and second swing blocks connected to the swing arm. The first weighting piece is carried on the first swing block. The second weighting piece is carried on the second swing block. The swing arm is swingable to move the second swing block to block and unblock the opening.

15 Claims, 5 Drawing Sheets

OSCILLATING POSITIVE EXPIRATORY PRESSURE DEVICE

CROSS-REFERENCE TO RELATED APPLICATIONS

This application claims priority of Taiwanese Patent Application No. 110121639, filed on Jun. 15, 2021.

FIELD

The disclosure relates to a positive expiratory pressure (PEP) device, more particularly to an oscillating positive expiratory pressure (OPEP) device.

BACKGROUND

As air pollution has worsened in many places around the world, environmental allergens have increased considerably, making modern people more susceptible to respiratory disorders including cystic fibrosis (CF) and chronic obstructive pulmonary disease (COPD), which cause excessive secretions in their lungs and tracheas. Coughing should loosen secretions and subsequently expel them from the trachea of an average healthy person. In those with respiratory problems, however, a single cough may be unlikely to dislodge an obstruction in the trachea. In these cases, medication and oscillating positive expiratory pressure (OPEP) therapy are used to treat secretion accumulation. OPEP therapy uses a conventional OPEP device (such as an Acapella device) to open clogged tracheas and loosen secretions by oscillating vibrations of expiratory air pressure during the expiration of a user, allowing the user to cough them out and clear lung obstruction.

The conventional OPEP device, which controls the user's expiration resistance using a magnet, is currently used for therapeutic treatment. However, the structure of this device is relatively complex and bulky, and it isn't easy to clean.

SUMMARY

Therefore, the object of the disclosure is to provide an oscillating positive expiratory pressure device that can alleviate at least one of the drawbacks associated with the abovementioned prior art.

An oscillating positive expiratory pressure device includes a housing, a top cover, and an oscillating unit. The housing includes a bottom wall and a surrounding wall that extends upwardly from the bottom wall. The bottom wall has an inclined enclosing surface that extends downwardly and that terminates at an opening. The top cover is connected to the surrounding wall, and cooperates with the bottom wall and the surrounding wall to define an accommodating space. The oscillating unit is swingably connected to the housing and is disposed within the accommodating space. The oscillating unit includes a swing member, a first weighting piece, and a second weighting piece. The swing member includes a swing arm, a first swing block connected to one end of the swing arm, and a second swing block connected to another end of the swing arm and adjacent to the opening. The first weighting piece is carried on the first swing block. The second weighting piece is carried on the second swing block. The swing arm is swingable to move the second swing block to block and unblock the opening.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
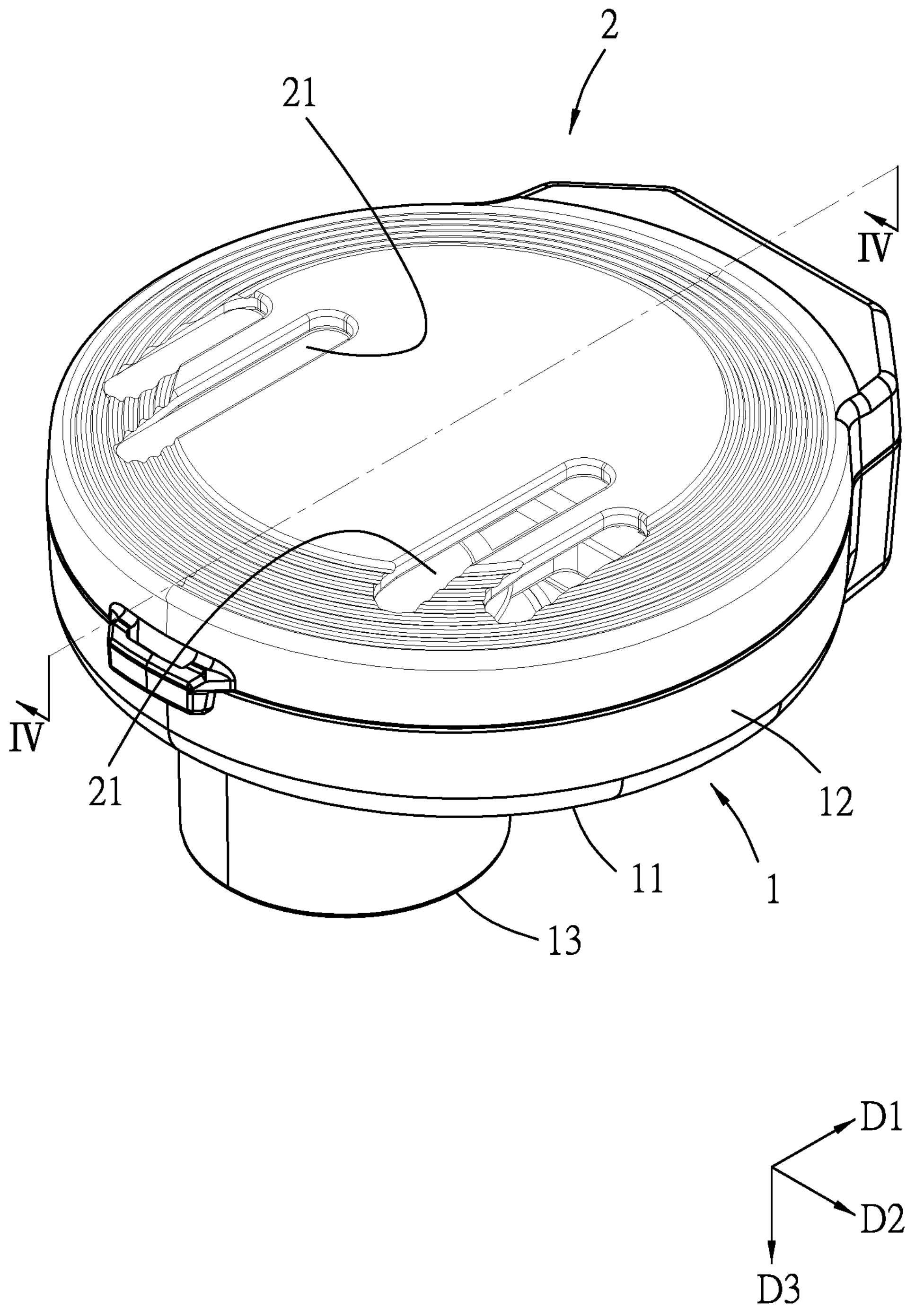
FIG. 1 is a perspective view of an embodiment of an oscillating positive expiratory pressure device according to the disclosure.
Figure 2:
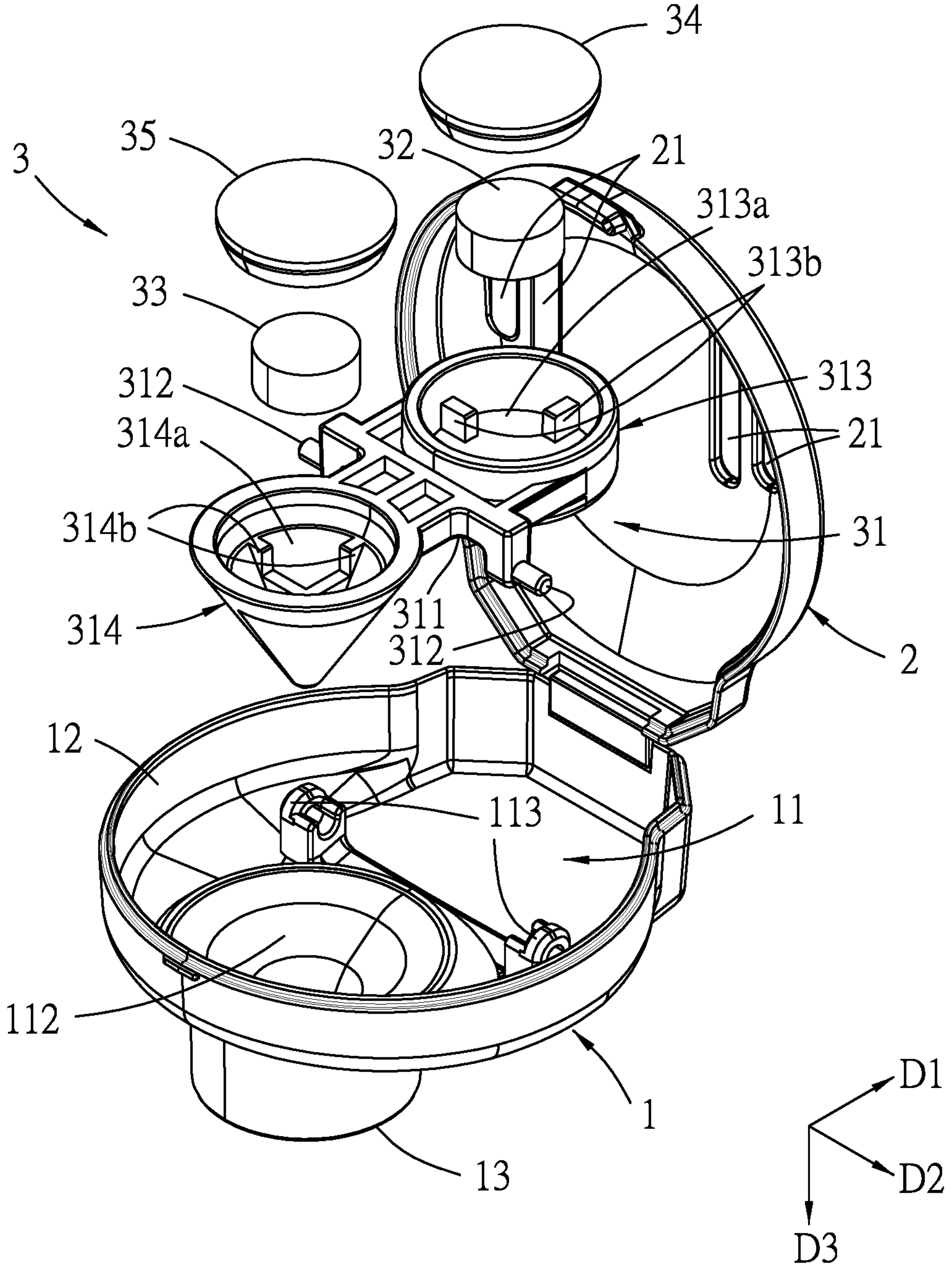
FIG. 2 is a partly exploded perspective view of the embodiment.

As shown in FIGS. 1 and 2, the embodiment of the oscillating positive expiratory pressure device as claimed in the present disclosure can be used to help a user in loosening secretions attached to the tracheas so that the user can then cough them out. The oscillating positive expiratory pressure device includes a housing 1, a top cover 2 and an oscillating unit 3.

Figure 3:
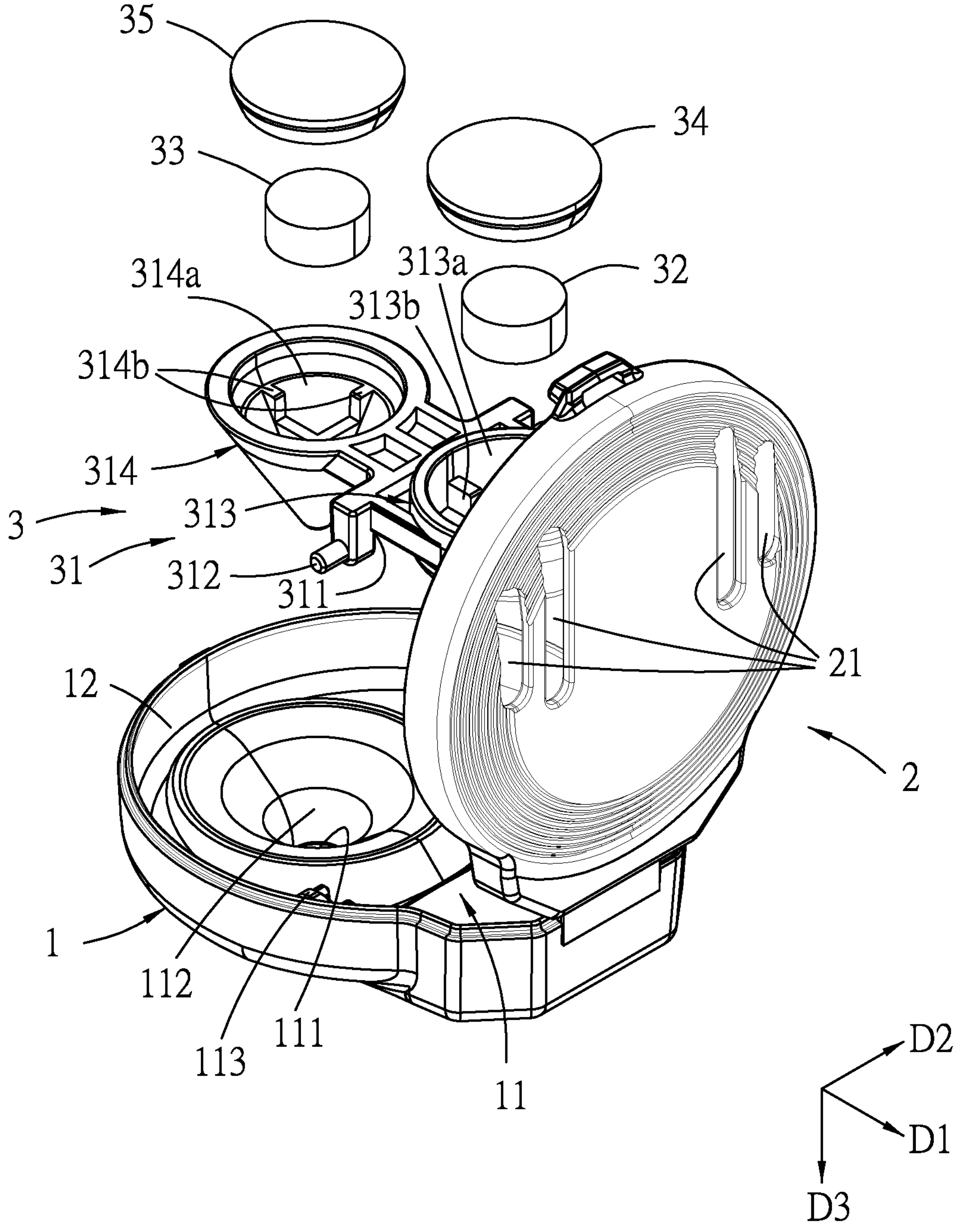
FIG. 3 is a partly exploded perspective view of the embodiment from another perspective.
Figure 4:
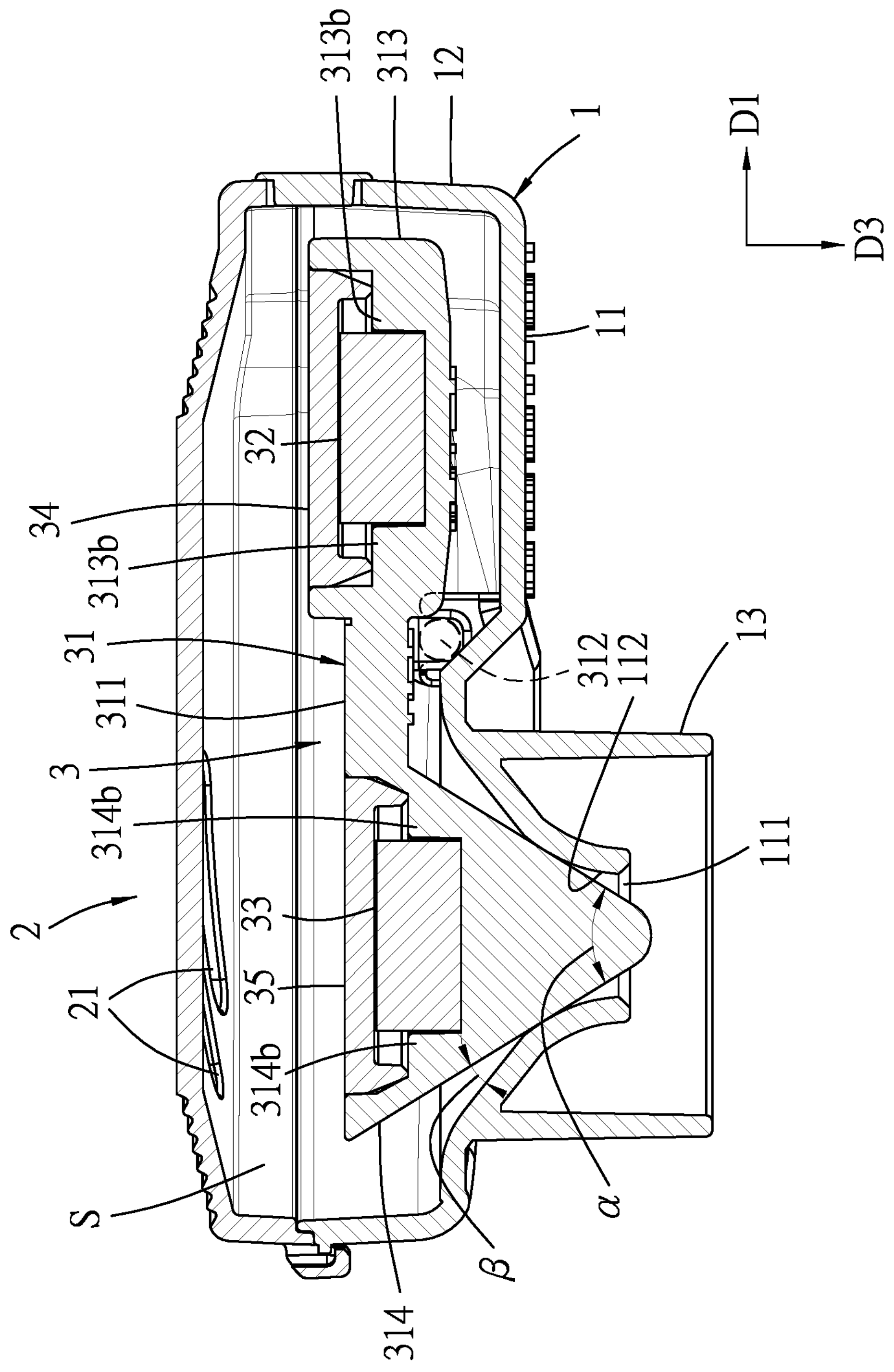
FIG. 4 is a cross-sectional view taken along line IV-IV in FIG. 1, illustrating an oscillating unit in a closed position.

Referring to FIGS. 2 to 4, the housing 1 includes a bottom wall 11, a surrounding wall 12 extending upward from the bottom wall 11 along an up-down direction (D3), and an input tube 13 extending downwardly from the bottom wall 11 along the up-down direction (D3). The bottom wall 11 has an inclined enclosing surface 112 that is substantially funnel-shaped, that extends downwardly from the bottom wall 11, that terminates at an opening 111 and that is surrounded by the input tube 13. The bottom wall 11 further has two support brackets 113 extending upright. A cross-sectional width of the inclined enclosing surface 112 decreases in the up-down direction (D3), as shown in FIG. 4. The inclined enclosing surface 112 has a curved portion adjacent to the opening 111. The oscillating unit 3 is swingably mounted on the support brackets 113 of the bottom wall 11. The top cover 2 is connected to the surrounding wall 12, and cooperates with the surrounding wall 12 and the bottom wall 11 to define an accommodating space (S). The top cover 2 is formed with four vent holes 21 extending along a front-rear direction (D1) and spaced apart from each other. The vent holes 21 are positioned corresponding to the opening 111. The total area of the vent holes 21 occupies less than 50% of the area of the top cover 2. In this embodiment, the total area of the vent holes 21 is less than 5 square centimeters, but the area is not limited to this figure in other embodiments. The number and extension direction of the vent holes 21 are also not limited to those mentioned above.

The oscillating unit 3 is disposed within the accommodating space (S), and includes a swing member 31 including a swing arm 311 that extends in the front-rear direction (D1), a first swing block 313 that is connected to one end of the swing arm 311, and a second swing block 314 that is connected to another end of the swing arm 311 and that is adjacent to the opening 111. The oscillating unit 3 further includes a first weighting piece 32 that is carried on the first swing block 313, a second weighting piece 33 that is carried on the second swing block 314, a first lid 34 that is disposed over the first weighting piece 32, and a second lid 35 that is disposed over the second weighting piece 33. and the swing member 31 further includes two rotary pins 312 protruding laterally and respectively from opposite sides of the swing arm 31 parallel to a left-right direction (D2) and being held respectively by the support brackets 113 to form a rotating axis of the swing member 31 so that the swing member 31 can swing about the rotating axis. The first swing block 313 is substantially cylindrical-shaped, and has a first accommodating groove 313*a* accommodating the first weighting piece 32 therein, and four first retaining ribs 313*b* disposed in the first accommodating groove 313*a* and abutting against the first weighting piece 32. The second swing block 314 is substantially conical and tapers toward the opening 111, and has a second accommodating groove 314*a* accommodating the second weighting piece 33 therein, and four second retaining ribs 314*b* disposed in the second accommodating groove 314*a* and abutting against the second weighting piece 33. The first lid 34 and the second lid 35 respectively close the first accommodating groove 313*a* and the second accommodating groove 314*a*. The first weighting piece 32 and the second weighting piece 33 can be positioned in a tightly fitted manner in the first accommodating groove 313*a* and the second accommodating groove 314*a* through the first retaining ribs 313*b* and the second retaining ribs 314*b*.

Figure 5:
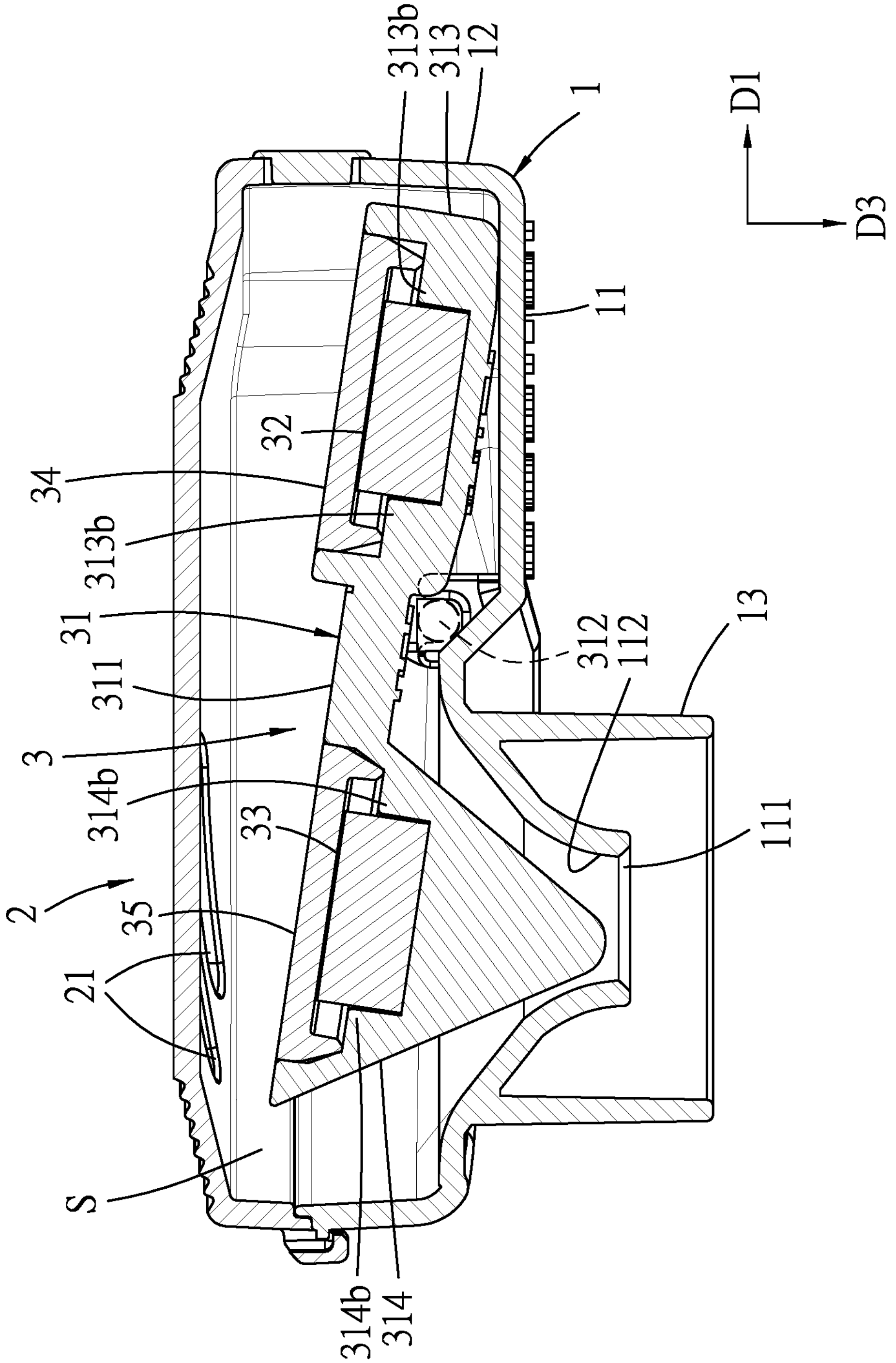
FIG. 5 is a cross-sectional view similar to FIG. 4, illustrating the oscillating unit in an open position.

Referring to FIGS. 4 and 5, the oscillating unit 3 can swing about the rotary pins 312 relative to the bottom wall 11 of the housing 1, between closed and open positions. In the closed position, the second swing block 314 is inserted into the opening 111 with a lateral surface thereof being in contact with the inclined enclosing surface 112, thereby blocking the opening ill, as shown in FIG. 4. The oscillating unit 3 can swing upwardly from the closed position to the open position. During the conversion of the oscillating unit 3 from the closed position to the open position, the first swing block 313 swings downwardly to contact the bottom wall 11, and the second swing block 314 swings upwardly to be separated from the inclined enclosing surface 112 and unblock the opening 111, as shown in FIG. 5.

Each of the first weighting piece 32 and the second weighting piece 33 has a density greater than 2, and the preferred weight of the first and second weighting pieces 32, 32 ranges between 1 to 4 grams. To achieve a generally smooth oscillation of the oscillating unit 3, the first and second weighting pieces 32, 33 should preferably be of the same weight.

A cross section of the second swing block 314 along an axis of the second swing block 314 in the up-down direction (D3) has two opposite sides that form an included angle (α) therebetween. The included angle (α) affects the Coanda Effect at the inclined enclosing surface 112, and is preferably between 53 degrees and 73 degrees. Actual measurements show that an incorporated angle between 58 degrees and 68 degrees offers more desirable operational performance. On the other hand, when the oscillating unit 3 is in the closed position, an included angle (β) defined between each of the opposite sides of the cross section of the second swing block 314 along the axis of the second swing block 314 and the inclined enclosing surface 112 will affect the swing of the oscillating unit 3, and ranges between 10 and 30 degrees. More preferably the included angle (β) ranges between 16 to 24 degrees.

Flow Rate and Weighting Piece Test

The aforementioned preferred angle setting is shown in Table 1. The test is carried out by simulating an average adult with an expiratory flow rate ranging from 5 to 30 liters per minute and a static expiratory pressure of 8 to 18 $cmH_2O$. It has been recognized by those skilled in the art that the most successful treatment is obtained when the pressure change of the expiratory airflow, corresponding to the amplitude of airflow oscillation, ranges between 5 to 20 $cmH_2O$, with a frequency of airflow oscillation between 10 to 40 Hz. A to D listed in the column head of Table 1 are the different settings of the included angle (β) for the present oscillating positive expiratory pressure device, which are 16.75 degrees, 20 degrees, 23.3 degrees, and 26.5 degrees in sequence. The different weights of the first and second weighting pieces 32 and 33 (unit: grams) are listed in each column of the second row labeled "weighting piece." The varying frequencies of airflow oscillation (Hz, oscillations per second) at different simulated expiratory flow rates (5 LPM to 30 LPM as listed in the left-hand column) are given in Table 1. Different frequencies of airflow oscillation will be achieved by varying different selected weights at different simulated expiratory flow rates, as given in Table 1. A lower oscillating frequency is more likely to be achieved by increasing in the selected weight of the weighting pieces. Table 2 depicts the varying amplitudes of the simulated user's expiratory airflow oscillation (unit: $cmH_2O$) obtained by varying the selected weight of the weighting pieces. It can be determined from the data in the table that the amplitude of the expiratory airflow oscillation is more likely to grow with an increase of the selected weight of the weighting piece.

TABLE 1

| | A | | | | B | | | | C | | | | D | | | |
|---|---|---|---|---|---|---|---|---|---|---|---|---|---|---|---|---|
| | weighting piece | | | | | | | | | | | | | | | |
| Hz | 1 | 2 | 3 | 4 | 1 | 2 | 3 | 4 | 1 | 2 | 3 | 4 | 1 | 2 | 3 | 4 |
| 5 LPM | 10.8 | 11.0 | 11.0 | 10.4 | 10.4 | 11.0 | 10.2 | 9.2 | 10.0 | 9.3 | 9.0 | 9.3 | 10.6 | 11.2 | 11.5 | 11.8 |
| 10 LPM | 9.1 | 9.2 | 8.9 | 9.0 | 8.8 | 8.4 | 8.4 | 8.0 | 9.0 | 8.2 | 7.0 | 7.9 | 9.0 | 8.8 | 8.2 | 8.9 |
| 25 LPM | 15.0 | 13.7 | 12.0 | 11.3 | 14.1 | 12.7 | 11.2 | 9.4 | 14.4 | 11.7 | 10.7 | 10.2 | 13.4 | 12.1 | 8.8 | 10.7 |
| 30 LPM | 16.8 | 14.8 | 13.5 | 13.2 | 15.2 | 13.6 | 12.2 | 10.8 | 15.8 | 12.7 | 11.8 | 10.8 | 14.0 | 13.1 | 9.7 | 13.0 |

TABLE 2

| | A | | | | B | | | | C | | | | D | | | |
|---|---|---|---|---|---|---|---|---|---|---|---|---|---|---|---|---|
| | weighting piece | | | | | | | | | | | | | | | |
| P-A | 1 | 2 | 3 | 4 | 1 | 2 | 3 | 4 | 1 | 2 | 3 | 4 | 1 | 2 | 3 | 4 |
| 5 LPM | 2.9 | 3.2 | 2.9 | 3.3 | 3.0 | 3.1 | 3.2 | 3.7 | 2.9 | 3.7 | 3.5 | 4.0 | 2.9 | 2.9 | 2.1 | 1.8 |
| 10 LPM | 5.2 | 6.0 | 6.7 | 7.0 | 5.3 | 5.8 | 6.0 | 7.5 | 5.3 | 6.2 | 6.9 | 7.3 | 5.3 | 6.0 | 6.3 | 6.1 |

TABLE 2-continued

| | A | | | | B | | | | C | | | | D | | | |
|---|---|---|---|---|---|---|---|---|---|---|---|---|---|---|---|---|
| | weighting piece | | | | | | | | | | | | | | | |
| P-A | 1 | 2 | 3 | 4 | 1 | 2 | 3 | 4 | 1 | 2 | 3 | 4 | 1 | 2 | 3 | 4 |
| 25 LPM | 10.0 | 11.8 | 13.8 | 14.4 | 10.2 | 11.6 | 13.6 | 15.4 | 9.4 | 11.8 | 13.7 | 14.8 | 9.0 | 11.4 | 12.6 | 12.6 |
| 30 LPM | 9.9 | 12.8 | 15.4 | 15.0 | 10.6 | 13.0 | 15.0 | 17.4 | 10.0 | 13.0 | 14.6 | 16.8 | 10.6 | 12.2 | 16.0 | 13.2 |

In order to reduce the overall volume of the present oscillating positive expiratory pressure device, the center of gravity of the first weighting piece 32, the rotary pins 312, and the center of gravity of the second weighting piece 33 are configure not to be collinear in the front-rear direction (D1). In addition, to maximize the weight gain efficiency of the first weighting piece 32 and the second weighting piece 33 in balance with the second swing block 314, a ratio between a distance in the front-rear direction (D1) between the center of gravity of the first weighting piece 32 and the axis passing through the rotary pins 312 and a distance in the front-rear direction (D1) between the center of gravity of the second weighting piece 33 and the axis passing the rotary pins 312 is 5:7, which is 10 mm:14 mm in this embodiment but not limited to this in other embodiments.

The operation of the present oscillating positive expiratory pressure device is as follows: a mouthpiece (not shown) is attached to the input tube 13 of the housing 1 for the user to hold in the mouth. Every time the user exhales, the expiratory airflow passing through the mouthpiece and the input tube 13 will push the second swing block 314 to move upward, making the oscillating unit 3 swing from the closed position where the second swing block 314 blocks the opening 111 to the open position where the second swing block unblocks the opening 111. The curved portion of the inclined enclosing surface 112 is slightly convex curved. When the user's expiratory airflow passes, the Coanda effect will be produced, reducing the air pressure applied against the second swing block 314, thus decreasing the upward acceleration thereof. When the weight of the second swing block 314 and the second weighting piece 33, combined with the Coanda effect of the airflow over the curved portion of the inclined enclosing surface 112, overcomes the expiratory air pressure applied to the second swing block 314, the second swing block 314 descends to block the opening 111 until the user's next expiration. The vibration induced in the expiratory airflow helps loosen the secretions in the trachea of the user, especially in the bronchus, so the user can cough out the secretions. The oscillating swing movement of the oscillating unit 3 between the closed and open positions will continue to vibrate as the user exhales and produce vibrations in the expiratory airflow during operation. It can be appreciated that, since the oscillating frequency of the oscillating unit 3 can be changed by varying the weights of the first weighting piece 32 and the second weighting piece 33, the increase of weight of the first weighting piece 32 and the second weighting piece 33 will reduce the oscillating frequency produced by the oscillating unit 3. In addition, the oscillation frequency of the oscillating unit 3 can also be varied by changing the distance in the front-rear direction (D1) between the center of gravity of the first weighting piece 32 and the axis passing through the rotary pins 312 as well as the distance in the front-rear direction (D1) between the center of gravity of the second weighting piece 33 and the axis passing through the rotary pins 312, depending on the desired oscillating frequency produced by the oscillating unit 3.

It is noted that the first lid 34 and the second lid 35 in the present disclosure are primarily disposed to cover the exposed surface of the first weighting piece 32 and the second weighting piece 33 to prevent them from falling off during operation of the oscillating unit 3, and also provide a flat surface to reduce airflow disturbance and to reduce residual secretions, making it easier to clean. Moreover, in this embodiment, the first weighting piece 32 and the second weighting piece 33 are tightly fitted in the first accommodating groove 313*a* and the second accommodating groove 314*a* by the first retaining ribs 313*b* and the second retaining ribs 314*b*, respectively. In other embodiments, the amount of first and second retaining ribs 313*b* and 314*b* may be reduced. The first and second retaining ribs 313*b* and 314*b* may even be omitted entirely in other embodiments if the first accommodating groove 313*a* and the second accommodating groove 314*a* are made slightly smaller than the first weighting piece 32 and the second weighting piece 33, such that the first weighting piece 32 and the second weighting piece 33 can tightly fit in the first accommodating groove 313*a* and the second accommodating groove 314*a*.

The present oscillating positive expiratory pressure device can also be used in conjunction with a spray device as disclosed in Taiwanese Patent No. 1706797. When in use, the input tube 13 of housing 1 can be connected to a mouthpiece (not shown) that communicates with the spray device for the user to hold in the mouth. The present oscillating positive expiratory pressure device is actuated by expiration during the breath cycle. It causes a vibration of the expiratory air pressure, making it easier to cough out secretions in the user's trachea. At the same time, a portion of the user's expiratory airflow is diverted through the mouthpiece to the spray device to temporarily deactivate the spray device. The spray device is activated when the user inhales while suspending the operation of the oscillating positive expiratory pressure device. Therefore, the spray device and the oscillating positive expiratory pressure device operate cyclically when breathing in and out.

In summary, the opening 111 of the present oscillating positive expiratory pressure device is capable of being blocked by the second swing block 314 of the oscillating unit 3 until the user's expiratory airflow lifts the second swing block 314 to unblock the opening 111. When the weight of the second swing block 314 and the second weighting piece 33, combined with the Coanda effect of the airflow over the curved portion of the inclined enclosing surface 112, overcomes the expiratory air pressure applied against the second swing block 314, the second swing block 314 will descend to block the opening 111 again; the vibration of expiratory airflow produced by the oscillating unit 3 can be transmitted to the user's trachea to expand and contract the user's trachea. Through the continuous action of the oscillating unit 3, the secretions adhering to the user's trachea will be loosened such that the user can cough the secretions out.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. An oscillating positive expiratory pressure device comprising:

- a housing including a bottom wall and a surrounding wall that extends upwardly from said bottom wall, said bottom wall having an inclined enclosing surface that extends downwardly and that terminates at an opening;
- a top cover connected to said surrounding wall, and cooperating with said bottom wall and said surrounding wall to define an accommodating space; and
- an oscillating unit swingably connected to said housing and disposed within said accommodating space, said oscillating unit including
  - a swing member that includes
    - a swing arm,
    - a first swing block connected to one end of said swing arm, and
    - a second swing block connected to another end of said swing arm, and adjacent to said opening,
  - a first weighting piece that is carried on said first swing block, and
  - a second weighting piece that is carried on said second swing block, said swing arm being swingable to move said second swing block to block and unblock said opening;
- wherein said second swing block is substantially conical and tapers toward said opening;
- wherein
- a cross section of said second swing block along an axis of said second swing block has two opposite sides that form an included angle therebetween ranging between 53 degrees and 73 degrees; and
- when said oscillating unit is in a closed position, an included angle defined between each of said opposite sides of the cross section of said second swing block along the axis of said second swing block and and said inclined enclosing surface ranges between 16 degrees and 24 degrees.

2. The oscillating positive expiratory pressure device as claimed in claim 1, wherein:

- said first swing block of said swing arm has a first accommodating groove accommodating said first weighting piece therein;
- said second swing block of said swing arm has a second accommodating groove accommodating said second weighting piece therein; and
- said oscillating unit further includes a first lid closing said first accommodating groove, and a second lid closing said second accommodating groove.

3. The oscillating positive expiratory pressure device as claimed in claim 2, wherein:

- said first swing block further has a plurality of first retaining ribs disposed in said first accommodating groove and abutting against said first weighting piece; and
- said second swing block has a plurality of second retaining ribs disposed in said second accommodating groove and abutting against said second weighting piece.

4. The oscillating positive expiratory pressure device as claimed in claim 1, wherein:

- said swing member further includes two rotary pins protruding laterally and respectively from opposite sides of said swing arm; and
- said bottom wall further has two support brackets holding said two rotary pins, respectively.

5. The oscillating positive expiratory pressure device as claimed in claim 4, wherein:

- said swing arm extends along a front-rear direction; and
- a ratio between a distance in the front-rear direction between a center of gravity of said first weighting piece and an axis passing through said rotary pins and a distance in the front-rear direction between a center of gravity of said second weighting piece and the axis passing through said rotary pins is 5:7.

6. The oscillating positive expiratory pressure device as claimed in claim 1, wherein said top cover is formed with a plurality of vent holes which occupy less than 50% of the area of said top cover.

7. The oscillating positive expiratory pressure device as claimed in claim 1, wherein each of said first weighting piece and said second weighting piece has a density greater than 2.

8. An oscillating positive expiratory pressure device comprising:

- a housing including a bottom wall and a surrounding wall that extends upwardly from said bottom wall, said bottom wall having an inclined enclosing surface that extends downwardly and that terminates at an opening;
- a top cover connected to said surrounding wall, and cooperating with said bottom wall and said surrounding wall to define an accommodating space; and
- an oscillating unit swingably connected to said housing and disposed within said accommodating space, said oscillating unit including
  - a swing member that includes
    - a swing arm,
    - a first swing block connected to one end of said swing arm, and
    - a second swing block connected to another end of said swing arm, and adjacent to said opening,
  - a first weighting piece that is carried on said first swing block, and
  - a second weighting piece that is carried on said second swing block, said swing arm being swingable to move said second swing block to block and unblock said opening; and wherein:

said first swing block of said swing arm has a first accommodating groove accommodating said first weighting piece therein;

said second swing block of said swing arm has a second accommodating groove accommodating said second weighting piece therein; and said oscillating unit further includes a first lid closing said first accommodating groove, and a second lid closing said second accommodating groove.

9. The oscillating positive expiratory pressure device as claimed in claim 8, wherein said second swing block is substantially conical and tapers toward said opening.

10. The oscillating positive expiratory pressure device as claimed in claim 9, wherein:

a cross section of said second swing block along an axis of said second swing block has two opposite sides that form an included angle therebetween ranging between 53 degrees and 73 degrees; and when said oscillating unit is in a closed position, an included angle defined between each of said opposite sides of the cross section of said second swing block along the axis of said second swing block and said inclined enclosing surface ranges between 10 degrees and 30 degrees.

11. The oscillating positive expiratory pressure device as claimed in claim 8, wherein:

said first swing block further has a plurality of first retaining ribs disposed in said first accommodating groove and abutting against said first weighting piece; and said second swing block has a plurality of second retaining ribs disposed in said second accommodating groove and abutting against said second weighting piece.

12. The oscillating positive expiratory pressure device as claimed in claim 8, wherein:

said swing member further includes two rotary pins protruding laterally and respectively from opposite sides of said swing arm; and said bottom wall further has two support brackets holding said two rotary pins, respectively.

13. The oscillating positive expiratory pressure device as claimed in claim 12, wherein:

said swing arm extends along a front-rear direction; and a ratio between a distance in the front-rear direction between a center of gravity of said first weighting piece and an axis passing through said rotary pins and a distance in the front-rear direction between a center of gravity of said second weighting piece and the axis passing through said rotary pins is 5:7.

14. The oscillating positive expiratory pressure device as claimed in claim 8, wherein said top cover is formed with a plurality of vent holes which occupy less than 50% of the area of said top cover.

15. The oscillating positive expiratory pressure device as claimed in claim 8, wherein each of said first weighting piece and said second weighting piece has a density greater than 2.

* * * * *